United States Patent [19]

Chia et al.

[11] Patent Number: 4,857,299

[45] Date of Patent: Aug. 15, 1989

[54] STABLE RADIODIAGNOSTIC PRODUCT

[75] Inventors: Han-Lie Chia, Reinach; Horia Popescu, Basel; Gabrielle Boehmer, Reinach, all of Switzerland

[73] Assignee: Solco Basel AG, Basel, Switzerland

[21] Appl. No.: 125,608

[22] Filed: Nov. 25, 1987

[51] Int. Cl.$^4$ .................... A61K 49/02; C07F 13/00; C07C 143/42
[52] U.S. Cl. ........................ 424/1.1; 534/14; 252/404; 252/400.62; 562/478; 260/512 R
[58] Field of Search .................... 424/1.1; 534/14; 252/404, 400.62; 562/478; 260/512 R

[56] References Cited

U.S. PATENT DOCUMENTS

| | | | |
|---|---|---|---|
| 4,229,427 | 10/1980 | Whitehouse | 424/1.1 |
| 4,440,738 | 4/1984 | Fawzi et al. | 424/1.1 |
| 4,451,451 | 5/1984 | Rimmer | 424/1.1 |

FOREIGN PATENT DOCUMENTS 1124390  8/1968  United Kingdom ................ 260/512

*Primary Examiner*—John S. Maples
*Attorney, Agent, or Firm*—Wenderoth, Lind & Ponack

[57] ABSTRACT

Stable injection solutions of radiodiagnostic aids ready for use are obtained by addition to the organ-or tissue-specific carrier, before, during or after the labeling with the pertechnetate, of a compound of the formula:

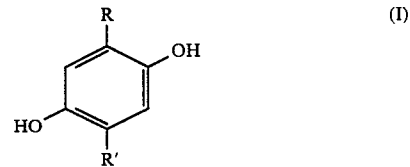

in which R denotes hydrogen, and R' denotes a sulpho- or a carboxymethyl group, or R and R' each denote a sulpho- or a carboxymethyl group, or a water-soluble salt thereof, as stabilizer. These compounds do not alter the specific organ or tissue distribution of the carrier.

17 Claims, No Drawings

STABLE RADIODIAGNOSTIC PRODUCT

The invention relates to stable products which are ready for use and labeled with the radionuclide Tc-99m for use as radiodiagnostic aids, to a process for the preparation thereof, and to agents for carrying out the process.

Skeletal scintigraphy with $^{99m}$Tc-methylenediphosphonate ($^{99m}$Tc-MDP) is a method which is nowadays indispensable for the diagnosis of pathological processes in bone. Its place in nuclear medicine has increased continuously in importance in recent years. In fact, because of its sensitivity, this method is used in programmed time intervals in the detection of disturbances of bone metabolism for the early diagnosis of bone metastases in the postoperative care of certain types of cancer.

Since several patients are referred each day to nuclear medical laboratories for skeletal scintigraphy and, on the other hand, the optimal interval between the administration of $^{99m}$Tc-MDP or similar products and the scintigraphy is 2 to 3 hours, it would be an advantage to have available a radiopharmaceutical which can be labeled early in the morning with a high level of radioactivity of $^{99m}$Tc-pertechnetate and from which it is possible to take throughout the day as many single doses as patients referred for scintigraphy.

Furthermore, there have evolved, especially in the USA, Great Britain and Holland, what are called "radiopharmacies". Normally they do not themselves carry out any nuclear medical investigations, but they do supply on a daily basis, to smaller hospitals, nuclear medical laboratories and private practices, single doses of products which are ready for injection. It is important for these centers to have at hand stable radiopharmaceuticals; they are then able to serve an extended circle of clients over a greater distance.

Now, as is known, injection solutions labeled with Tc-99m can be kept for only a limited time, in contrast to the lyophilisates composed of organ-specific carrier and reducing agent (for example tin(II) salt). Only a few hours after labeling, especially where the level of Tc-99m activity is high, the presence of free pertechnetate can be detected in the injection solution; this diminishes the quality of the products. This is because free pertechnetate accumulates in the stomach and in the thyroid, and in this way causes unnecessary exposure to radiation. Furthermore, it interferes with clear visualization of the target organs or tissues owing to a radiation background in the soft tissues.

The reversion of technetium ions to free pertechnetate derives from the oxidizing action of the residual oxygen which may be present in the solution, but especially from that of various radiolytic products, especially of radicals and peroxides; the latter are continuously formed in aqueous solution as a consequence of radiolysis. In turn, the presence of residual oxygen and even traces of heavy metal ions catalyzes radiolysis.

Our investigations of eluates from the Tc-99m generator have shown that the content of peroxides in eluates, which are in practice usually left to stand until used for the labeling of radiopharmaceuticals, increases over the course of time. Table 1 shows that the rate of formation of peroxides increases with the initial level of Tc-99m activity in the eluates (semi-quantitative peroxide determination using Merckoquant test strips, Merck Cat. No. 10011). The detection limit of the method is 1 ppm.

TABLE 1

| | Peroxide content (in ppm) of Tc-99m eluates from Tc-99m generators | | | | |
|---|---|---|---|---|---|
| Standing time after elution | 57.2 GBq (1546 mCi) | 41.5 GBq (1122 mCi) | 32.9 GBq (889 mCi) | 27.9 GBq (755 mCi) | 12.2 GBq (330 mCi) |
| 0–1 h | 0 | 0 | 0 | 0 | 0 |
| 3 h | 1 | 1 | 1 | — | — |
| 5 h | 3 | 1–3 | 1–3 | 1–2 | 0 |
| 8 h | —[1] | 3 | 3 | — | — |
| 26 h | — | — | — | 0–1 | 0 |
| 48 h | — | — | — | 0 | 0 |

[1] not determined

It has been proposed to stabilize the $^{99m}$Tc-labeled injection solutions by, inter alia, the use of various chemical substances and, in particular, of complexing agents. For example, cysteine [J. Nucl. Med. 22 (1981), 645], hydroquinone (U.S. Pat. No. 4,229,427), gentisyl alcohol (U.S. Pat. No. 4,232,000) and many other complex-forming compounds (U.S. Pat. No. 4,027,005) have been investigated in this respect.

It has been particularly recommended to use, on the one hand, reductic acids, especially ascorbic acid, its salts and esters (German Pat. Nos. 2,618,337, 2,619,382 and 2,660,424; U.S. Pat. Nos. 4,075,314, 4,440,738 and 4,504,462; Canadian Pat. No. 1,114,291), or, on the other hand, hydroxy- and aminobenzoic acids, in particular 2,5-dihydroxybenzoic acid or gentisic acid, and their salts (U.S. Pat. Nos. 4,233,284, 4,451,451 and 4,504,463; German Pat. No. 3,331,159; European Pat. No. 4,684; WO Pat. No. 85/3231). The complexing agents ascorbic acid and gentisic acid, and 4-aminobenzoic acid, have been used effectively in commercial radiopharmaceuticals.

However, the disadvantage associated with complexing agents is that they form complexes not only with tin(II) and tin(IV) ions which are present in excess but also with the $^{99m}$technetium ions likewise. These complexes are soluble in water and hence are distributed throughout the body and, in particular, in soft tissues, and in this way they generate a radiation background which diminishes the quality (sharpness) of the scintigraphic images. This is an undesired side effect which is common to the complexing agents when used as stabilizers.

An additional factor is that the organ distribution and the excretion of the complexes formed from the $^{99m}$technetium ions sometimes differ from those of the organ- or tissue-specific Tc-99m radiopharmaceuticals which have to be prepared. For example, cysteine or ascorbic acid diminishes the quality of the bone agent (pyrophosphate, diphosphonates) because Tc-99m-cysteine and Tc-99m-ascorbic acid undergo mainly renal excretion. N-(4-Aminobenzoyl)glutamic acid and N-(4-aminobenzoyl)aspartic acid in high concentration as stabilizers increase the renal excretion of the bone agent 2,3-dicarboxypropane-1,1-diphosphonic acid.

It has now been found, unexpectedly, that compounds of the formula

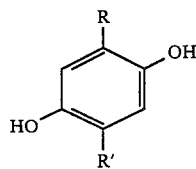

(I)

in which R denotes hydrogen, and R' denotes a sulpho- or carboxymethyl group, or R and R' each denote a sulpho- or a carboxymethyl group, and their water-soluble salts, exert an excellent stabilizing action, although they are not complexing agents, on $^{99m}$Tc-pertechnetate and the injection solutions prepared therefrom. This finding was all the more surprising because virtually all the compounds which have hitherto been proposed or used as stabilizers are complexing agents.

The above formula embraces specifically 2,5-dihydroxybenzenesulphonic acid, 2,5-dihydroxybenzene-1,4-disulphonic acid, 2,5-dihydroxyphenylacetic acid and 2,5-dihydroxy-4-carboxymethylphenylacetic acid. Particularly suitable water-soluble salts are the alkali metal and ammonium salts; the sodium salts are preferred.

The fact that these compounds and their water-soluble salts do not form stable or water-soluble complexes, either with transition metals or with heavy metals, in the physiologically tolerated pH range of about 4 to 9 is evident from the following experiment.

The compound to be tested is dissolved in water, and the solution is adjusted to a pH below 2 using dilute hydrochloric acid, and is mixed with a solution of SnF$_2$ or SnCl$_2$.2H$_2$O in 0.1N hydrochloric acid. The resulting solution is completely clear; as is known, stable solutions of tin(II) ions are obtained only in strongly acid or strongly alkaline medium (formation of stannite ions in the second case). The pH is then increased to a middling level by slow addition of dilute sodium hydroxide solution. If the solution remains clear, the compound has bound the tin(II) ions to form a complex; on the other hand, if turbidity develops (basic tin salts, tin hydroxide) no complex has been formed.

TABLE 2

| pH and appearance of aqueous solutions of tin(II) salts | | |
|---|---|---|
| Content in 10 ml of solution | pH | Appearance |
| 5 mg SnCl$_2$.2 H$_2$O | <2 | clear |
| | 2 to 12 | turbid |
| | >12 | clear |
| 4 mg SnF$_2$ 50 mg ascorbic acid | 4.7 | clear |
| 5 mg SnCl$_2$.2 H$_2$O 100 mg 1,2-dihydroxybenzene (catechol) | 7.6 | clear |
| 5 mg SnCl$_2$.2 H$_2$O 100 mg 1,2,3-trihydroxybenzene (pyrogallol) | 6.0 | clear |
| 4 mg SnF$_2$ 50 mg 2,5-dihydroxybenzoic acid (gentisic acid) | 6.5 | clear |
| 5 mg SnCl$_2$.2 H$_2$O 100 mg 1,2-dihydroxybenzene-3,5-disulphonic acid (Tiron) | 6.0 | clear |
| 5 mg SnCl$_2$.2 H$_2$O 100 mg 2,5-dihydroxybenzenesulphonic acid | 3.0 | turbid |
| 4 mg SnF$_2$ 50 mg 2,5-dihydroxybenzene-1,4-disulphonic acid | 3.5 | turbid |
| 5 mg SnCl$_2$.2 H$_2$O 100 mg 2,5-dihydroxyphenylacetic acid | 2.6 | turbid |

TABLE 2-continued

| pH and appearance of aqueous solutions of tin(II) salts | | |
|---|---|---|
| Content in 10 ml of solution | pH | Appearance |
| 5 mg SnCl$_2$.2 H$_2$O 100 mg 2,5-dihydroxy-4-carboxymethylphenylacetic acid | 4.3 | turbid |

It is evident from Table 2 that with complexing agents such as ascorbic acid, gentisic acid etc. the tin(II) ions form stable complexes which are soluble in weakly acid to weakly alkaline media.

Now the compounds of the formula (I) are readily soluble in water in the pH range from 2 to 9. Thus the turbidity found in this pH range can be explained only by there being no complexes formed by these compounds with the tin(II) ions; in this they contrast sharply with the customary stabilizers.

Nevertheless, addition of the said compounds in low concentration to Tc-99m-radiodiagnostic aids stabilizes them against the oxidizing action of the peroxides and free radicals which are formed over the course of time. Even after labeling with high Tc-99m activity (at least 5.5 GBq, 150 mCi) solutions of this type prove to be stable for several hours (at least 4 hours).

This action is illustrated in Table 3 by the example of the bone-specific carrier methylenediphosphonic acid (MDP). 20 mg portions of this compound are each dissolved in 1.0 ml of water and introduced into ampuls; then tin(II) fluoride and sodium pertechnetate and, where appropriate, a stabilizer in low concentration are added to the contents of the ampul. The content of free $^{99m}$Tc-pertechnetate is determined after 10 minutes and 5 and 8 hours, and is calculated as a % of the activity used for labeling. The determination is carried out by high-voltage radioelectrophoresis (HVE) on Whatman paper 1 with acetate buffer (0.04M; pH 6.5; 2,000 volt, 30 minutes) or by thin-layer radiochromatography (TLRC) on Whatman paper 31 ET with acetone as mobile phase.

TABLE 3

| Stabilizing action of the compounds (I) on $^{99m}$Tc-methylenediphosphonate | | | | |
|---|---|---|---|---|
| Contents of the ampul (beside 20 mg MDP in 1.0 ml water | Activity used for labelling | % content of free pertechnetate Determination by HVE | | |
| | | 10 min | 5 h | 8 h |
| Comparison product I | | | | |
| 0.8 mg tin(II) fluoride without stabilizer | 5.4–6.1 GBq (146–165 mCi) | 0 | 14.3 | —1 |
| Example 1 | | | | |
| 0.8 mg tin(II) fluoride 0.1 mg compound A,$^2$ dipotassium salt | " | 0 | 0 | — |
| Example 2 | | | | |
| 0.8 mg tin(II) fluoride 0.1 mg 2,5-dihydroxyphenylacetic acid | " | 0 | 3.8 | — |
| Example 3 | | | | |
| 0.8 mg tin(II) fluoride 0.2 mg compound A, dipotassium salt | (a) 6.8–7.9 GBq (185–210 mCi) | 0 | 0 | — |
| | (b) 10.7–11.4 GBq (290–310 mCi) | 0 | 0 | 4.5 |
| | (c) " | 0 | 0 | 0 |
| Comparison product II | | | | |
| 1.2 mg tin(II) fluoride | (a) 5.4–6.1 GBq | 0 | 8–10 | — |

TABLE 3-continued

Stabilizing action of the compounds (I) on $^{99m}$Tc-methylenediphosphonate

| Contents of the ampul (beside 20 mg MDP in 1.0 ml water | Activity used for labelling | % content of free pertechnetate Determination by HVE | | |
|---|---|---|---|---|
| | | 10 min | 5 h | 8 h |
| (50% more reducing agent) without stabilizer | (146–165 mCi) (b) 10.7–11.4 GBq (290–310 mCi) | 0 | 19–20 | 30–31 |

[1] not determined
[2] 2,5-dihydroxybenzene-1,4-disulphonic acid

It is evident that, in the absence of a stabilizer, free pertechnetate is detectable (14.3%) in the solution after only 5 hours, and that even increasing the content of tin(II) ions is unable to stabilize the solution (see comparison product I and comparison product II).

The concentration which suffices for stabilization is generally about 0.1 to 6 μM of the compounds of the formula (I); a concentration of 0.5 to 4 μM is usually preferred.

In the extremely low concentration mentioned, these compounds in fact prove to be distinctly superior, in respect of their stabilizing action, to the complexing agents hitherto used, as is evident in Table 4 from the content of free pertechnetate 8 hours after labeling. The amount of activity used for labeling in each case was 10.7–11.1 GBq (290–300 mCi), the amount of methylenediphosphonic acid was 20 mg in each case, and that of tin(II) fluoride was 0.8 mg in each case.

TABLE 4

Comparison of the action of various stabilizers

| Content of the ampul (besides 20 mg MDP and 0.8 mg SnF$_2$ in 1 ml water) | % content of free pertechnetate Determination by | | | |
|---|---|---|---|---|
| | HVE | | TLRC | |
| | 10 min | 8 h | 10 min | 8 h |
| Example 3 | | | | |
| 0.6 μM compound A,[1] dipotassium salt | 0 | 0–12 | 0 | 0–1 |
| Comparison product | | | | |
| III | | | | |
| 0.6 μM 4-aminobenzoic acid | 0 | 2–9 | 0 | 0–2 |
| IV | | | | |
| 3.6 μM 4-hydroxybenzoic acid | 0 | 6–15 | 0 | 3–5 |
| V | | | | |
| 3.6 μM 2,5-dihydroxybenzoic acid (gentisic acid) | 0 | 14–15 | 0 | 9–12 |

[1] 2,5-dihydroxybenzene-1,4-disulphonic acid

Similar results in respect of the stability of the injection solutions are obtained when other compounds are used as organ-specific or tissue-specific carrier in place of the methylenediphosphonic acid. Examples of these which may be mentioned are, for bone scintigraphy, water-soluble phosphates, polyphosphates and pyrophosphates and, in particular, organic phosphonic acid derivatives such as, inter alia, those listed in U.S. Pat. No. 4,229,427; for static and functional kidney investigation, for example diethylenetriaminepentaacetic acid, dimercaptosuccinic acid or a glucoheptonate; as hepatobiliary carriers those of the nitrilotriacetic acid monoanilide series such as the mono(2,6-dimethyl, 2,4,6-trimethyl, 2,6-diethyl, 2,6-diisopropyl or 4-butyl-)anilide and their halogen derivatives (HIDA derivatives); as well as particulate products, for example albumin macroaggregates and microspheres; for scintigraphy of the reticuloendothelial system colloidal products, for example the micro- and nanocolloids composed of human serum albumin, of sulphur or of rhenium; products composed of proteins, for example human serum albumin or fibrinogen; products composed of macrocyclic compounds, for example derivatives of mercaptoacetylglycylglycylglycine (MAG$_3$) and of similar tripeptides.

It ought to be emphasized in addition that the described stabilizing action is not achieved at the expense of, for example, the organ- or tissue-specificity; the latter is in fact guaranteed to the full extent, as is evident from Table 5 in the example of $^{99m}$Tc-methylenediphosphonate (MDP). Strict adherence to the organ or tissue distribution which is specific to the particular carrier in the injection solutions of radiodiagnostic aids stabilized according to the invention is, of course, a principal condition for their practical use.

In order to determine the distribution of the radioactivity in the individual organs and tissues, the injection solutions are each administered intravenously to groups of 5 rats, the experimental animals are sacrificed and dissected after 2 hours, the isolated organs and tissues are combined according to their nature, and the radioactivity thereof is measured. It is expressed for the individual organs and tissues as a % of the total recovered activity ± standard deviation.

TABLE 5

Organ distribution of $^{99m}$Tc-methylenediphosphonate with and without stabilizer[1]

| Composition of the solution (1.0 ml) | 20 mg MDP 0.8 mg SnF$_2$ without stabilizer | 20 mg MDP 0.8 mg SnF$_2$ 0.2 mg 2.5-dihydroxybenzene-1.4-disulphonic acid (Example 3) | 20 mg MDP 0.8 mg SnF$_2$ 0.2 mg 2.5-dihydroxyphenylacetic acid |
|---|---|---|---|
| Blood | 0,40 ± 0,05 | 0,44 ± 0,08 | 0,46 ± 0,18 |
| Lungs | 0.05 ± 0,01 | 0,06 ± 0,01 | 0,05 ± 0,01 |
| Liver | 0,22 ± 0,05 | 0,23 ± 0,05 | 0,15 ± 0,04 |
| Spleen | 0,01 ± 0,00 | 0,01 ± 0,00 | 0,01 ± 0,00 |
| Kidneys | 0,77 ± 0,15 | 1,11 ± 0,60 | 0,60 ± 0,07 |
| Stomach | 0,05 ± 0,01 | 0,06 ± 0,00 | 0,04 ± 0,00 |
| Intestinal tract | 0,31 ± 0,06 | 0,53 ± 0,18 | 0,34 ± 0,07 |
| Bone | 52,31 ± 2,04 | 57,25 ± 2,50 | 52,24 ± 1,92 |

TABLE 5-continued

Organ distribution of $^{99m}$Tc-methylenediphosphonate with and without stabilizer[1]

| | | | |
|---|---|---|---|
| Muscle | 0,90 ± 0,16 | 1,15 ± 0,39 | 0,73 ± 0,18 |
| Thyroid | 0,00 ± 0,00 | 0,00 ± 0,00 | 0,00 ± 0,00 |
| Urine and bladder | 44,97 ± 2,05 | 39,18 ± 3,28 | 42,88 ± 0,58 |
| Total | 99.99 ± 2,90 | 100.02 ± 4,19 | 97.50 ± 2.09 |

[1] As % of recovered activity

On wide-ranging comparison with the compounds which have hitherto been proposed or used for the stabilization of $^{99m}$Tc-labeled products, the compounds of the formula I are distinguished, at very low concentration, by an efficacy which is greater or the same, and, on the other hand, they make it possible to obtain scintigraphic images whose quality is not diminished by a radiation background.

Thus, the invention makes available stable $^{99m}$Tc-labeled products which are ready for use and which are intended for use as radiodiagnostic aids and contain (a) a substance which acts as an organ- or tissue-specific carrier and is labeled with the radionuclide Tc-99m, and (b) a compound of the formula (I), or a water-soluble salt thereof, in an amount which suffices to stabilize the products against oxidizing effects.

The products according to the invention are prepared by addition to the substance (a) which is intended as or acts as carrier, before, during or after the labeling thereof with the radionuclide Tc-99m, of the compound designated (b) above as stabilizer in a concentration which is lower than the concentration of carrier.

The labeling itself is carried out by addition of a pertechnetate and exposure to a reducing agent, such as a tin(II) salt, an iron(II) salt or a chromium(II) salt, or sodium borohydride or sodium dithionite; tin(II) chloride or tin(II) fluoride is preferably used as reducing agent.

The three process variants and preferred embodiments of the invention are described in more detail hereinafter.

I. Addition of the Stabilizer Before Labeling

The compound chosen as stabilizer is added to a solution of the carrier and of the reducing agent; it is preferable for the solution of the three components then to be lyophilized. The lyophilisate thus contains the organ-specific or tissue-specific carrier, the reducing agent and the compound intended as stabilizer; it represents a preferred agent for carrying out the process which is defined above, and is advantageously marketed under vacuum in a vial.

It then suffices, in the laboratory or in the hospital, to mix the lyophilisate with the calculated amount of Tc-99m eluate from the generator to obtain the radiodiagnostic aid which is ready for use and is stable for several hours.

II. Addition of the Stabilizer During Labeling

In the second process variant, the compound intended as stabilizer is present in the eluate which contains the Tc-99m-pertechnetate and is intended to be used to label the carrier. An advantageous embodiment of the invention comprises the said compound being marketed in solid form and under vacuum in a vial which is intended to receive the eluate from the Tc-99m generator, the eluate being introduced into the vial, and the solution of eluate and stabilizer being used to label the carrier, with the assistance of a reducing agent.

However, it is also possible to introduce the stabilizer into the Tc-99m generator itself, before removing the eluate containing radioactive pertechnetate, and to obtain in this way an eluate which already contains the stabilizer. In this embodiment, the stabilizer is likewise added to the carrier during labeling.

III. Addition of the Stabilizer After Labeling

The third process variant comprises addition of the compound chosen as stabilizer to the product which is already labeled with Tc-99m, which is carried out by addition of an aqueous solution or of a lyophilisate of the said compound.

EXAMPLE 1

1.0 g of methylenediphosphonic acid (MDP) is introduced into 25 ml of distilled water. The pH of the acid solution is adjusted to 7.0 with 2N NaOH. Subsequently, 4.0 ml of 1% strength tin(II) fluoride solution in 0.1N HCl, and 1.0 ml of a 0.5% strength solution of dipotassium 2,5-dihydroxybenzene-1,4-disulphonate in distilled water are added with stirring. The solution prepared in this way is adjusted to pH 6.5 with 1N HCl or 1N NaOH, and is diluted with distilled water to a final volume of 50 ml. After sterilization by filtration through a 0.2µ sterile filter, the filtrate is lyophilized in 1.0 ml portions in ampuls.

Ampul contents:
 20 mg of MDP
 0.8 mg of tin(II) fluoride
 0.1 mg of dipotassium 2,5-dihydroxybenzene-1,4-disulphonate Findings on analysis: see Table 3

EXAMPLE 2

An injection solution of the following composition is prepared as in Example 1:

Ampul contents:
 20 mg of MDP
 0.8 mg of tin(II) fluoride
 0.1 mg of 2,5-dihydroxyphenylacetic acid Findings on analysis: see Table 3

EXAMPLE 3

2.0 g of methylenediphosphonic acid (MDP) are introduced into 80 ml of distilled water. 80 mg of solid tin(II) fluoride are dissolved in the resultant acid solution (pH 1.8). Then 21 mg of solid dipotassium 2,5-dihydroxy-1,4-benzenedisulphonate are added to the solution and dissolved by stirring. After the pH has been adjusted to 7.0 with 2N sodium hydroxide solution, the solution is diluted with distilled water to a final volume of 100 ml and then filtered through a 0.2µ sterile filter. The filtrate is lyophilized in 1 ml portions in ampuls.

Ampul contents:
 20 mg of MDP 0.8 mg of SnF$_2$
0.2 mg (0.6 μM) of dipotassium 2,5-dihydroxybenzene-1,4-disulphonate
Findings on analysis: see Table 3

Comparison Products I and II

For comparison with Examples 1 to 3, products are prepared as in Example 1 but without addition of a stabilizer and are designated comparison product I and II hereinafter.

|  | I | II |
|---|---|---|
| Ampul contents: MDP | 20 mg | 20 mg |
| SnF$_2$ | 0.8 mg | 1.2 mg |

Comparison Products III, IV and V

For comparison with Example 3, products are prepared as in Example 1 but containing known stabilizers. The ampul contents (in 1.0 ml) are stated below; the findings on analysis are to be found in Table 4.

| III | IV | V |
|---|---|---|
| mg of MDP | 20 mg of MDP | 20 mg of MDP |
| 0.8 mg of SnF$_2$ | 0.8 mg of SnF$_2$ | 0.8 mg of SnF$_2$ |
| 0.08 mg of 4-amino-benzoic acid (0.6 μM) | 0.5 mg of 4-hydroxy-benzoic acid (3.6 μM) | 0.55 mg of 2,5-dihydroxy-benzoic acid (gentisic acid) (3.6 μM) |

EXAMPLE 4

5 ml of freshly eluted $^{99m}$Tc eluate with an activity of 17.17 GBq (464 mCi) are added to 0.2 ml of a 0.1% strength solution of the dipotassium salt of 2,5-dihydroxybenzene-1,4-disulphonic acid (compound A) in water.

The peroxide content in the $^{99m}$Tc eluate prepared in this way is determined semiquantitatively using Merckoquant test strips for peroxide tests (Merck Cat. No. 10011). The determinations are carried out after various times have elapsed following treatment of the Tc-99m eluate with the said disulphonic acid.

| Time elapsed | 10 min | 5 h | 8 h |
|---|---|---|---|
| Peroxide content | 0 ppm | 0 ppm | 0 ppm |

EXAMPLE 5

The $^{99m}$Tc eluate from Example 4 which has been treated with the dipotassium salt of 2,5-dihydroxybenzene-1,4-disulphonic acid (compound A) is used for labeling comparison product I-composed of 20 mg of MDP and 0.8 mg of tin(II) fluoride in 1.0 ml. The content of free pertechnetate in the labeled MDP solutions is determined by thin-layer radiochromatography on Whatman paper 31 ET using acetone as mobile phase, and is expressed as a % of the activity used for labeling. The results are to be found in Table 6.

TABLE 6

| | Content of free pertechnetate as % of the labeling activity | |
|---|---|---|
| Stabilizer | 0.064 mg of compound A | 0.128 mg of compound A |
| Activity of the $^{99m}$Tc eluate | 5.437 GBq (147 mCi) | 10.7 GBq (289 mCi) |
| Time elapsed after labeling | | |
| 10 min | 0% | 0% |
| 5 h | 0% | 0% |
| 8 h | 6.6% | 2.4% |

EXAMPLE 6

2.0 g of methylenediphosphonic acid (MDP) are dissolved in 80 ml of distilled water. Under a nitrogen atmosphere, 80 mg of solid tin(II) fluoride are added to the MDP solution. After the pH has been adjusted to 5.0 with 2N NaOH, 82 mg of 2,5-dihydroxybenzenesulphonic acid are dissolved therein. The solution is adjusted to a pH of 7.0 by further addition of 2N NaOH, and is diluted with distilled water to a final volume of 100 ml. The solution is filtered through a 0.2μ sterile filter, and the filtrate is lyophilized in 1 ml portions in ampuls.

Ampul contents:
    20.0 mg MDP
    0.8 mg tin(II) fluoride
    0.82 mg (3.6 μM) 2,5-dihydroxybenzenesulphonic acid
Findings on analysis:
    radiochromatography: see Table 7
    organ distribution: see Table 8

EXAMPLE 7

A product of the following composition is prepared as in Example 6.
Ampul contents:
    20.0 mg of MDP
    0.8 mg of tin(II) fluoride
    0.6 mg (3.6 μM) of 2,5-dihydroxyphenylacetic acid
Findings on analysis:
    radiochromatography: see Table 7
    organ distribution: see Table 8

EXAMPLE 8

A product of the following composition is prepared as in Example 6.
Ampul contents:
    20.0 mg of MDP
    0.8 mg of tin(II) fluoride
    0.81 mg (3.6 μM) of 2,5-dihydroxy-4-carboxymethylphenylacetic acid
Findings on analysis:
    radiochromatography: see Table 7
    organ distribution: see Table 8

TABLE 7

| | Content of free pertechnetate as % of the labeling activity | | |
|---|---|---|---|
| | Example 6 | Example 7 | Example 8 |
| Labeling activity (per ampul) | 12,000 MBq (324 mCi) | 11,000 MBq (297 mCi) | 11,000 MBq (297 mCi) |
| HVE finding[1] | | | |
| 10 min | 0 | 0 | 0-1 |
| 5 h | 0 | 0 | 0-1 |
| 8 h | 0-1 | 0-1 | 0-1 |

TABLE 7-continued

| Content of free pertechnetate as % of the labeling activity | | | |
|---|---|---|---|
| | Example 6 | Example 7 | Example 8 |
| RC finding[2] | | | |
| 10 min | 0 | 0 | 0 |
| 5 h | 0 | 0 | |
| 8 h | 0–1 | 0–1 | 0–1 |

[1] By high-voltage radioelectrophoresis on Whatman paper 1 in acetate buffer (0.04 M; pH 6.5; 30 min at 2,000 V).
[2] By radiochromatography on Gelman ITLC-SG in acetone.

TABLE 8

| Organ distribution of the $^{99m}$Tc-methylenediphosphonate[1] (rats, n = 5, 2 h after i.v. administration) | | | |
|---|---|---|---|
| | Example 6 | Example 7 | Example 8 |
| Labelling activity (per ampul) | 12,000 MBq (324 mCi) | 11,000 MBq (297 mCi) | 11,000 MBq (297 mCi) |
| Blood | 0.47 ± 0.16 | 0.58 ± 0.06 | 0.62 ± 0.22 |
| Lungs | 0.06 ± 0.01 | 0.05 ± 0.03 | 0.08 ± 0.03 |
| Liver | 0.21 ± 0.07 | 0.29 ± 0.05 | 0.27 ± 0.08 |
| Spleen | 0.02 ± 0.00 | 0.02 ± 0.00 | 0.02 ± 0.00 |
| Kidneys | 0.68 ± 0.14 | 1.31 ± 0.34 | 0.81 ± 0.41 |
| Stomach | 0.08 ± 0.03 | 0.11 ± 0.02 | 0.25 ± 0.04 |
| Intestinal tract | 0.45 ± 0.09 | 0.43 ± 0.05 | 0.51 ± 0.29 |
| Bone | 41.80 ± 4.91 | 53.54 ± 7.95 | 46.07 ± 0.48 |
| Muscle | 0.96 ± 0.25 | 1.16 ± 0.13 | 1.00 ± 0.29 |
| Thyroid | 0.00 ± 0.00 | 0.00 ± 0.00 | 0.01 ± 0.00 |
| Urine | 54.18 ± 7.64 | 38.67 ± 4.83 | 45.37 ± 1.32 |
| Total | 98.91 | 96.16 | 95.01 |

[1] Mean as % of the labeling activity used

We claim:

1. A stable product for use as a radiodiagnostic aid, which comprises
   (a) an organ-specific or tissue-specific carrier which is labeled with radionuclide Tc-99m, and
   (b) for stabilization of the product a compound of the formula:

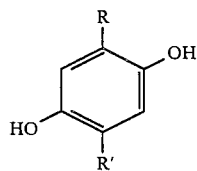

(I)

in which R denotes hydrogen, and R' denotes a sulpho- or carboxymethyl group, or R and R' each denote a sulpho- or a carboxymethyl group, or a water-soluble salt thereof, the compound (b) being present in a concentration which is less than that of the carrier.

2. A stable product as claimed in claim 1 wherein 2,5-dihydroxybenzene-1,4-disulphonic acid or its sodium salt is used as the compound of the formula I.

3. A stable product as claimed in claim 1 wherein an alkali metal or an ammonium salt is used as water-soluble salt.

4. A stable product according to claim 3 wherein the alkali metal is sodium.

5. A stable product according to claim 3 wherein 2,5-dihydroxybenzene-1,4-disulphonic acid or its sodium salt is used as the compound of the formula I.

6. A stable product as claimed in claim 1, wherein the compound used for stabilization is present in a concentration of 0.1 to 6.0 μM.

7. A stable product according to claim 6 wherein the concentration is 0.5 to 4.0 μM.

8. A stable product as claimed in claim 1, wherein the carrier is a substance suitable for bone scintigraphy.

9. A stable product according to claim 8 wherein the substance suitable for bone scintigraphy is a pyrophosphate or a diphosphonic acid derivative.

10. A stable product according to claim 9 wherein the diphosphonic acid derivative is a member selected from the group consisting of methylenediphosphonic acid, hydroxymethylenediphosphonic acid and 2,3-dicarboxy-propane-1,1-diphosphonic acid.

11. A stable product as claimed in claim 1, wherein the carrier is a substance suitable for static or functional kidney investigation.

12. A stable product according to claim 11 wherein the substance suitable for static or functional kidney investigation is a member selected from the group consisting of diethylenetriaminepentaacetic acid, dimercaptosuccinic acid, a glucoheptonate, and a derivative or mercaptoacetylglycylglycylglycine.

13. A stable product as claimed in claim 1, wherein the carrier is a substance suitable for scintigraphy of the hepatobiliary system.

14. A stable product according to claim 13 wherein the substance suitable for scintigraphy of the heptobiliary system is a derivative from the nitrilotriacetic acid monoanilide series.

15. A stable product as claimed in claim 1, wherein the carrier is a substance suitable for scintigraphy of the reticuloendothelial system.

16. A stable product according to claim 15 wherein the substance suitable for scintigraphy of the reticuloendothelial system is a colloidal product.

17. A stable product according to claim 16 wherein the colloidal product is a micro- or nanocolloid composed of human serum albumin, sulphur or rhenium.

* * * * *